United States Patent [19]

Warnant et al.

[11] 4,136,195

[45] Jan. 23, 1979

[54] INSECTICIDAL CYCLOPROPANE CARBOXYLATES

[75] Inventors: Julien Warnant, Neuilly-sur-Seine; Jacques Prost-Maréchal, Paris; Philippe Cosquer, Saint-Denis, all of France

[73] Assignee: Roussel Uclaf, Paris, France

[21] Appl. No.: 789,842

[22] Filed: Apr. 22, 1977

[30] Foreign Application Priority Data

Apr. 23, 1976 [FR] France .............................. 76 12094

[51] Int. Cl.$^2$ ..................... A01N 9/20; C07C 121/ 66
[52] U.S. Cl. ............................. 424/304; 260/465 D
[58] Field of Search .................. 260/465 D; 424/304

[56] References Cited

U.S. PATENT DOCUMENTS

| | | |
|---|---|---|
| 3,835,176 | 9/1974 | Matsuo et al. ................ 260/465 D |
| 3,973,036 | 8/1976 | Hirano et al. ..................... 424/304 |
| 4,024,163 | 5/1977 | Elliott et al. ............... 260/465 D X |

Primary Examiner—Dolph H. Torrence
Attorney, Agent, or Firm—Hammond & Littell

[57] ABSTRACT

The novel esters, (R) α-cyano-3-phenoxybenzyl 2,2-dimethyl-3R-(2,2-dichlorovinyl)-cyclopropane-1R-carboxylate and (S) α-cyano-3-phenoxybenzyl 2,2-dimethyl-3R-(2,2-dichlorovinyl)-cyclopropane-1R-carboxylate, having insecticidal properties.

3 Claims, No Drawings

INSECTICIDAL CYCLOPROPANE CARBOXYLATES

STATE OF THE ART

French Pat. No. 2,240,914 describes synthetic insecticides of the pyrethrin type.

OBJECTS OF THE INVENTION

It is an object of the invention to provide the novel (R) and (S) α-cyano-3-phenoxybenzyl 2,2-dimethyl-3R-(2,2-dichlorovinyl)-cyclopropane-1R-carboxylates.

It is another object of the invention to provide novel insecticidal composition and to provide a novel method of killing insects.

These and other objects and advantages of the invention will become obvious from the following detailed description.

THE INVENTION

The novel compounds of the invention are selected from the group consisting of (R) α-cyano-3-phenoxybenzyl 2,2-dimethyl-3R-(2,2-dichlorovinyl)-cyclopropane-1R-carboxylate and (S) α-cyano-3-phenoxybenzyl 2,2-dimethyl-3R-(2,2-dichlorovinyl)-cyclopropane-1R-carboxylate.

The (S) α-cyano-3-phenoxybenzyl 2,2-dimethyl-3R-(2,2-dichlorovinyl)-cyclopropane-1R-carboxylate may be prepared from (R) α-cyano-3-phenoxybenzyl 2,2-dimethyl-3R-(2,2-dichlorovinyl)-cyclopropane-1R-carboxylate or a mixture of the (R) and (S) isomer of α-cyano-3-phenoxybenzyl 2,2-dimethyl-3R-(2,2-dichlorovinyl)-cyclopropane-1R-carboxylate in nonequimolecular proportions [designated hereafter as (R+S) dichloro ester] or a racemic mixture (R,S). The process comprises reacting the ester of the (R) alcohol or the (R+S) dichloro ester or the ester of the racemic (R,S) alcohol with a basic agent selected from the group consisting of ammonium hydroxide, primary, secondary and tertiary amines, quaternary ammonium compounds, ions exchange resins of a basic nature, high molecular weight liquid amines and a catalytic amount of a strong base in one or more solvents in which the (S) isomer is insoluble and the (R) isomer is soluble and then isolating from the reaction medium the ester of the (S) alcohol thus insoluble.

The basic agent used in the process is preferably selected from the group consisting of ammonium hydroxide, triethylamine, diethylamine, morpholine, pyrrolidine, piperidine and a strong base selected from the group consisting of sodium hydroxide, potassium hydroxide, alkali metal alcoholates, alkali metal amides and alkali metal hydrides. However, the list of said bases is not intended to be limiting and other bases of analogous strength may be used such as diisopropylamine, ephedrine, triethylenediamine and catalytic amounts of potassium tert.-butylate or sodium isopropylate.

Other basic agents include benzylamine, n-butylamine, sec-butylamine, tetrabutylammonium hydroxide and ions exchange resins of a strong basic character comprising quaternary ammoniums or amines. Resins of this type are sold under the tradenames Dowex and Amberlite such as Dowex AGIX8, Amberlite IRA 400 or Amberlite IR 45. Also useful as the basic agent are high molecular weight liquid amines which are insoluble in water such as the "liquid Amberlites" which are commerically sold such as liquid Amberlites of the type LA1 or LA2.

The solvent or mixture of solvents used in the process are preferably selected from the group consisting of acetonitrile, alkanols, mixtures of alkanols and petroleum ether, notably mixtures of an alkanol and pentane, hexane or heptane and most preferred are acetonitrile, propanol, isopropanol, straight and branch chained butanols and mixtures of the said alkanols with essence G, essence B, essence C, essence E, pentane, hexane or heptane. Isopropanol is particularly interesting for the transformation of the process.

It is evident that the term "insoluble" for the esters of the (S) alcohol and "soluble" for the ester of the (R) alcohol are taken in their current acceptance. In the solvents used in the process, the ester of the (S) alcohol presents a certain solubility which must be weak enough to obtain a good yield, taking into account the volume of solvent used. In practice, the solvent or mixture of solvents as well as the volume of the solvents permit the obtaining of a weight yield of at least 80% of the ester of the (S) alcohol. The preceding list of solvents and solvent mixtures is not intended to be limiting as other solvent systems may be used.

The esters of the (R) alcohol are in general very soluble in the solvents used in the process described above and a limited volume of solvent permits total solubilization.

The reaction temperature influences the rate of the reaction and the reaction time is a function of the temperature and the nature of the base used.

The racemic (R,S) α-cyano-3-phenoxybenzyl 2,2-dimethyl-3R-(2,2-dichlorovinyl)-cyclopropane-1R-carboxylates may be separated by chromatography to isolate (R) α-cyano-3-phenoxybenzyl 2,2-dimethyl-3R-(2,2-dichlorovinyl)-cyclopropane-1R-carboxylate.

(S) α-cyano-3-phenoxybenzyl 2,2-dimethyl-3R-(2,2-dichlorovinyl)-cyclopropane-1R-carboxylate has the greater insecticidal activity and is particularly useful in the agricultural field for combatting insects. For example, the said product is effective against aphis, larvae of Lepidoptera and coleoptera and is equally useful as a household insecticide for flies or mosquitoes. Experimental tests have shown the product to be effective against domestic flies and larvae of Spodoptera Littoralis.

The insecticidal compositions of the invention are comprised of an insecticidally effective amount of at least one compound of the group consisting of (R) α-cyano-3-phenoxybenzyl 2,2-dimethyl-3R-(2,2-dichlorovinyl)-cyclopropane-1R-carboxylate and (S) α-cyano-3-phenoxybenzyl 2,2-dimethyl-3R-(2,2-dichlorovinyl)-cyclopropane-1R-carboxylate and an inert carrier. The compositions may preferably contain 0.005 to 10% by weight of the active compounds and may contain one or more other pesticidal agents. The compositions may be in the form of powders, granules, suspensions, emulsions, solutions, aerosol compositions, combustible tapes, coils, or other classically used preparation for the use of compounds of this nature.

Examples of the inert carriers of the compositions of the invention are a vehicle and/or a non-ionic surface active agent to ensure a uniform dispersion of the substance making up the composition. The vehicle may be a liquid such as water, alcohol, hydrocarbons, other organic solvents or a mineral, animal or vegetable oil or a powdered solid such as talc, clays, silicates, kieselguhr or a combustible solid such as tabu powder (or pyrethrum residue).

To increase the insecticidal activity, the compositions may also contain a classic synergist for pyrethrum compounds such as 1-(2,5,8-trioxadodecyl-2-propyl-4,5-methylenedioxy)-benzene (or piperonyl butoxide), N-(2-ethyl heptyl)-bicyclo-[2,2,1]-5-heptene-2,3-dicarboximide and piperonylbis-2-(2'-n-butoxyethoxy)-ethyl acetal (tropital).

The novel method of the invention of combatting insects comprises contacting the insects with an insecticidally effective amount of at least one compound of the group consisting of (R) α-cyano-3-phenoxybenzyl 2,2-dimethyl-3R-(2,2-dichlorovinyl)-cyclopropane-1R-carboxylate and (S) α-cyano-3-phenoxybenzyl 2,2-dimethyl-3R-(2,2-dichlorovinyl)-cyclopropane-1R-carboxylate. The preferred compound is the ester of the (S) alcohol.

In the following examples there are described several preferred embodiments to illustrate the invention. However, it is to be understood that the invention is not intended to be limited to the specific embodiment.

EXAMPLE 1

10 g of (R,S) α-cyano-3-phenoxybenzyl 2,2-dimethyl-3R-(2,2-dichlorovinyl)-cyclopropane-1R-carboxylate with a specific rotation of $[\alpha]_D^{20} = +16.5°$ (c = 10% in benzene) were chromatographed over silica gel and elution with an 85-15 petroleum ether (Bp = 40°-70° C.) -isopropyl ether mixture yielded 3 g of (R) α-cyano-3-phenoxybenzyl 2,2-dimethyl-3R-(2,2-dichlorovinyl)-cyclopropane-1R-carboxylate with a specific rotation of $[\alpha]_D^{20} = -31°$ (c = 1% in benzene) and $-21.5°$ (c = 1% in chloroform).

120 ml of isopropanol and then 9 ml of a 22° Be aqueous ammonium hydroxide solution were added to 60 g of the said (R) α-cyano-3-phenoxybenzyl 2,2-dimethyl-3R-(2,2-dichlorovinyl)-cyclopropane-1R-carboxylate and the mixture was stirred at 0° C. for 48 hours. The mixture was vacuum filtered and the solid product was washed with 30 ml of isopropanol at $-20°$ C. and was dried to obtain 48.5 g of (S) α-cyano-3-phenoxybenzyl 2,2-dimethyl-3R-(2,2-dichlorovinyl)-cyclopropane-1R-carboxylate melting at 60° C. and having a specific rotation $[\alpha]_D^{20} = +66°$ (c = 1% in benzene) and $+34°$ (c = 1% in chloroform).

EXAMPLE 2

1200 ml of isopropanol were added to 600 g of (R,S) α-cyano-3-phenoxybenzyl 2,2-dimethyl-3R-(2,2-dichlorovinyl)-cyclopropane-1R-carboxylate with a specific rotation of $[\alpha]_D^{20} = +16.5°$ (c = 10% in benzene) and then 90 ml of 22° Be ammonium hydroxide solution cooled to 0° C. were added thereto. The mixture was stirred for 48 hours at 0° C. and was then vacuum filtered. The recovered product was washed with 300ml of isopropanol at $-20°$ C. and was dried to obtain 485 g of (S) α-cyano-3-phenoxybenzyl 2,2-dimethyl-3R-(2,2-dichlorovinyl)-cyclopropane-1R-carboxylate melting at 60° C. and having a specific rotation of $[\alpha]_D^{20} = +66°$ (c = 1% in benzene) and $+34°$ (c = 1% in chloroform).

Analysis: $C_{22}H_{19}O_3NCl_2$; molecular weight = 416.28
Calculated: %C 63.48; %H 4.60; %N 3.36; %Cl 17.03;
Found: 63.7 4.6 3.4 17.1.

EXAMPLE 3

An insecticidal composition was prepared from 25 g/l of (S) α-cyano-3-phenoxybenzyl 2,2-dimethyl-3R-(2,2-dichlorovinyl)-cyclopropane-1R-carboxylate, 10 g/l of 2,6-ditert.-butyl-p-cresol, 50 g/l of Emcol H 300B, 20 g/l of Emcol H 500B and 786 g/l of Supersol [a commercial mixture of aromatic solvents]. The Emcol products are surface active agents which are mixtures of calcium salts of alkyl benzene sulfonates (anionic part) and polyoxyethylene ethers (non-ionic part).

INSECTICIDAL ACTIVITY

A. Activity against houseflies

The insecticidal tests were effected on domestic flies of mixed sexes and a topical application of 1 μl of acetone solution of (S) α-cyano-3-phenoxybenzyl 2,2-dimethyl-3R-(2,2-dichlorovinyl)-cyclopropane-1R-carboxylate (product A) to the dorsal thorax of the flies was effected 0.50 flies were used for each test and the result were determined as the $LD_{50}$, dose at which 50% of the flies were dead 24 hours after treatment. The results are reported in Table I.

TABLE I

| Dose in ng of product A | % dead after 24 hours | $LD_{50}$ |
|---|---|---|
| 5 | 93.3 | |
| 3.75 | 83.2 | |
| 2.5 | 68.0 | 1.6 ng |
| 1.25 | 34.5 | |
| 0.625 | 10.0 | |

The results of Table I show that the product A has a very high insecticidal activity against houseflies.

B. Activity against Spodoptera Littoralis larvae

This test was effected by topical application of 1 μl of an acetone solution of product A on the dorsal thorax of each larva and for each test, 15 caterpillers of Spodoptera Littoralis in the 4th larva stage were used. After treatment, the individuals were placed in an artificial nutritive media (Poitot medium) and the number of dead caterpillers was determined 24 and 48 hours after the treatment to determine the $LD_{50}$ dose. The results are reported in Table II.

TABLE II

| Dose of A in ng | % dead after 24 h | % dead after 48 h | $LD_{50}$ at 48 h |
|---|---|---|---|
| 1.25 | 95.6 | 97.8 | |
| 0.625 | 80.0 | 82.2 | 0.3 ng |
| 0.3125 | 48.9 | 62.2 | |
| 0.1562 | 20.5 | 27.3 | |

Various modifications of the compounds and method of the invention may be made without departing from the spirit or scope thereof and it should be understood that the invention is to be limited only as defined in the appended claims.

We claim:
1. (S) α-cyano-3-phenoxy-benzyl 2,2-dimethyl-3R-(2,2-dichlorovinyl)-cyclopropane-1R-carboxylate.
2. An insecticidal composition comprising an insecticidally effective amount of (S) α-cyano-3-phenoxybenzyl 2,2-dimethyl-3R-(2,2-dichlorovinyl)-cyclopropane-1R-carboxylate and an inert carrier.
3. A method of combatting insects comprising contacting insects with an insecticidally effective amount of (S) α-cyano-3-phenoxybenzyl 2,2-dimethyl-3R-(2,2-dichlorovinyl)-cyclopropane-1R-carboxylate.

* * * * *